United States Patent [19]

Antonacci et al.

[11] Patent Number: 5,244,724
[45] Date of Patent: Sep. 14, 1993

[54] SELF-BONDED FIBROUS NONWOVEN WEBS HAVING IMPROVED SOFTNESS

[75] Inventors: Paul N. Antonacci, Smyrna; Delores R. Morris, Powder Springs; Peter W. Pascavage, Marietta; Steven M. Pruitt, Powder Springs, all of Ga.

[73] Assignee: Amoco Corporation, Chicago, Ill.

[21] Appl. No.: 880,494

[22] Filed: May 8, 1992

[51] Int. Cl.$^5$ .............................................. D04H 1/58
[52] U.S. Cl. .................................. 428/288; 428/289; 428/290; 428/287; 428/284; 428/913
[58] Field of Search .................. 252/8.6, 8.8; 428/288, 428/289, 290, 296, 287, 284, 903

[56] References Cited

U.S. PATENT DOCUMENTS

| | | | |
|---|---|---|---|
| 4,041,203 | 8/1977 | Brock et al. | 428/286 |
| 4,296,165 | 10/1981 | Kakar et al. | 428/289 |
| 4,840,738 | 6/1989 | Hardy et al. | 252/8.8 |
| 5,073,436 | 12/1991 | Antonacci et al. | 428/286 |

*Primary Examiner*—Patrick J. Ryan
*Assistant Examiner*—N. Edwards
*Attorney, Agent, or Firm*—Stephen L. Hensley; Frank J. Sroka

[57] ABSTRACT

A uniform basis weight self-bonded, fibrous nonwoven web having improved antistatic, softness and retention of water resistance in the presence of antistatic agents and composites comprising the nonwoven web useful for applications in the hygiene, healthcare, agriculture and other markets.

7 Claims, No Drawings

SELF-BONDED FIBROUS NONWOVEN WEBS HAVING IMPROVED SOFTNESS

FIELD OF THE INVENTION

This invention relates to uniform basis weight self-bonded, fibrous nonwoven webs having improved antistatic and softness properties and to products comprising such nonwoven webs useful for product applications in hygiene, medical, healthcare and agricultural markets.

BACKGROUND OF THE INVENTION

Uniform basis weight self-bonded nonwoven webs and a process for making such webs are disclosed in U.S. patent application Ser. No. 556,353, now U.S. Pat. No. 5,173,356, filed on Jul. 20, 1990, in the name of G. M. Eaton, et.al., assigned to the present assignee. Composites of such self-bonded nonwoven webs with materials such as meltblown fabric, woven fabric, porous film and net-like webs such as those designated CLAF® and available from Amoco Nisseki CLAF, Inc., are disclosed, respectively, in U.S. Pat. No. 5,073,436, U.S. patent application Ser. No. 805,579, filed Dec. 10, 1991, in the name of A. W. Stahle, et al., U.S. patent application Ser. No. 601,519, filed Oct. 23, 1990, in the name of W. H. Stover, and U.S. patent application Ser. No. 602,519, now U.S. Pat. No. 5,182,162, filed Oct. 24, 1990, in the name of F. G. Andrusko, each assigned to the present assignee.

These self-bonded nonwoven webs provide desirable properties of uniform basis weight and coverage and may be used as nonwoven webs by themselves or in combination with other materials in the form of composites. However, for applications wherein such self-bonded nonwoven webs can come into contact with a person's skin, it has been found desirable that these self-bonded webs have improved softness and antistatic properties.

Plastics, having insulative properties, are quite receptive to static electricity and typically do not dissipate static charge unless modified. Additives or modifiers which can be added to plastic melts or applied to plastics to prevent the buildup of electrostatic charges on plastic surfaces of articles made from such articles are referred to as "antistatic agents" or "antistats". Various antistat compositions are disclosed in the patents discussed below.

U.S. Pat. No. 3,580,735 discloses incorporating at least one antistatic agent such as quaternary ammonium salts, glycerides or fatty acid amides with at least one inorganic modifier and treating shaped articles with an antistatic agent for external use, such as a vinyl polymer containing an alkyl, carboxyl, glycidyl or sulphone group.

Japanese Patent No. 60-058444 discloses polyolefin compositions having 0.05 to 1.0 parts by weight of alkyl amines and/or alkylamides and 0.1 to 2.0 parts by weight of glycerine monoesters such as glycerine monostearate and linolic acid monoglyceride wherein such compositions have excellent antistatic properties and which, even when heat molded, high speed injection molded or oriented, do not lose the antistatic effect.

Belgium Patent No. 901310 discloses polypropylene compositions for fiber production containing synergistic mixtures of glycerol monostearate and ethoxylated tertiary amine.

Czechoslovakian Patent No. 8601268 discloses glycerol monostearate as an antistatic agent for polyolefins such as polypropylene fibers.

U.S. Pat. No. 4,041,203 discloses a nonwoven fabric-like material comprising a web of substantially continuous and randomly deposited, molecularly oriented filaments of a thermoplastic polymer having an average filament diameter in excess of 12 microns and an integrated mat of discontinuous, thermoplastic polymeric microfibers having an average fiber diameter up to about 10 microns and a softening temperature of about 10° to 40° C. less than the softening temperature of the continuous filaments. The disclosed laminates are treated with antistatic compositions in order to reduce surface resistivity to below about $1 \times 10^{12}$ ohms/square.

U.S. Pat. No. 5,071,699 discloses antistatic flexible fabric material formed from woven, axially oriented polypropylene yarn wherein the fabric has a coating on one or both sides of the fabric of a flexible thermoplastic polymer containing about 0.2 to 8 wt% of a polyol ester of a $C_{10}$ to $C_{28}$ fatty acid. The polypropylene yarn used to form the fabric may optionally also contain a lesser amount of the polyol ester of a $C_{10}$ to $C_{28}$ fatty acid.

When present on thermoplastic self-bonded nonwoven webs, static electricity can create undesirable effects such as dust pickup, interference during processing of such webs, static cling, sparking, and the like. In view of these undesirable effects, there is a need for uniform basis weight self-bonded, fibrous nonwoven webs having improved antistatic properties and whereby these nonwoven webs and composites comprising such webs have a reduced clinging effect and elimination of spark discharge and are less attractive to dust and lint. It is also desirable that for applications having human skin contact the self-bonded webs prepared from polypropylene-based thermoplastic resins have improved softness. Likewise, it is desirable especially in composite applications that such polypropylene-based webs which have antistatic agents present retain their as-formed water resistance properties as measured by hydrostatic resistance and water impact penetration.

Accordingly, it is an object of this invention to provide uniform basis weight self-bonded, fibrous nonwoven web having improved antistatic and surface resistivity properties.

Another object of this invention is to provide a uniform basis weight self-bonded, fibrous nonwoven web having improved antistatic and softness properties comprising a plurality of substantially continuous polymeric filaments wherein the polymeric filaments comprise a polyol ester of a monocarboxylic acid having 10 to 28 carbon atoms and a thermoplastic.

A still further object of this invention is to provide a composite product having antistatic properties, softness and retention of water resistance properties comprising at least one layer of a uniform basis weight self-bonded, fibrous nonwoven web comprising a plurality of substantially randomly disposed, substantially continuous polymeric filaments comprising glycerol monostearate and a thermoplastic selected from the group consisting of polypropylene, ethylene-propylene random copolymer, a blend of polypropylene and polybutene, and a blend of polypropylene and linear low density polyethylene wherein said web has a Basis Weight Uniformity Index of 1.0±0.05 determined from average basis weights having standard deviations of less than 10% and said web is adhered to at least one layer of a material selected from the group consisting of porous film, impervious film, woven fabric, polymeric foam product and nonwoven fabric such as meltblown fabric, spunbond fabric and carded web fabric.

Summary Of The Invention

The objects of this invention are provided in a uniform basis weight self-bonded, fibrous nonwoven web having improved antistatic properties comprising a plurality of substantially randomly disposed, substantially continuous polymeric filaments comprising an effective amount of an internal antistatic agent in combination with a thermoplastic wherein said web has a Basis Weight Uniformity Index of 1.0±0.05 determined from average basis weights having standard deviations of less than 10%. In another aspect, the invention provides a uniform basis weight self-bonded, fibrous nonwoven web having improved softness and antistatic properties comprising a plurality of substantially randomly disposed, substantially continuous polymeric filaments comprising an effective amount of glycerol monostearate and a thermoplastic selected from the group consisting of polypropylene, ethylene-propylene random copolymer, high density polyethylene, low density polyethylene, linear low density polyethylene, a blend of polypropylene and polybutene, and a blend of polypropylene and linear low density polyethylene wherein said web has a Basis Weight Uniformity Index of 1.0±0.05 determined from average basis weights having standard deviations of less than 10% and a surface resistivity of about $1.0 \times 10^{13}$ ohms/square or less. In still another aspect, the invention provides a composite product having improved antistatic and softness properties together with the retention of water resistant properties in the presence of antistatic agents comprising at least one layer of a uniform basis weight self-bonded, fibrous nonwoven web comprising a plurality of substantially randomly disposed, substantially continuous polymeric filaments comprising glycerol monostearate and a thermoplastic selected from the group consisting of polypropylene, ethylene-propylene random copolymer, a blend of polypropylene and polybutene, and a blend of polypropylene and linear low density polyethylene wherein said web has a Basis Weight Uniformity Index of 1.0±0.05 determined from average basis weights having standard deviations of less than 10% and said web is adhered to at least one layer of a material selected from the group consisting of porous film, impervious film, woven fabric, polymeric foam product and nonwoven fabric.

DETAILED DESCRIPTION OF THE INVENTION

Plastic materials including self-bonded, fibrous nonwoven webs are generally receptive to static electricity charge buildup and do not dissipate such static charge unless modified.

In this invention, a sufficient amount of antistatic agent is incorporated internally into the thermoplastic resin used in making self-bonded nonwoven webs such that the surface resistivity of the nonwoven web and of the composites made from such webs is $1.0 \times 10^{13}$ ohms/square or less. In one embodiment, glycerol monostearate is incorporated into polyolefin polymers such as polypropylene and such polymers are used in the production of self-bonded nonwoven webs which exhibit improved antistatic and softness properties. Such webs can in turn be adhered to other materials such as films, foam products, woven and nonwoven fabrics to form composites having improved antistatic and softness properties together with the retention of water resistance properties in the presence of antistatic agents.

Antistatic agents or antistats can generally be incorporated with thermoplastics by either internal or external means. External means of adding antistatic agents include solutions of molecules such as quaternary ammonium salts in the presence of carrier material such as fluorochemical emulsions, mineral oil and the like. Such external means added antistatic agents can be applied to the surface of thermoplastics by well-known methods such as dipping, coating, spraying and the like.

Internal means for incorporating antistatic agents into thermoplastic are typically one of two types with one type being conductive fillers such as carbon black, carbon fiber or metals compounded into the resin to form conductive paths. The second type can be a material which, with limited compatibility in the thermoplastic resin matrix, migrates to the surface of the thermoplastic resin. At the surface, hydrophilic groups attract ambient moisture to provide a path for dissipating the static electricity charge. Internal antistats can be added to thermoplastics via known means such as compounding extruders during manufacture of the thermoplastic resin in the production plant or as a separate compounding step. The antistatic agents are added in amounts and proportions sufficient so that they bloom to the surface at a rate sufficient to provide the desired antistatic property, but not so great that the surface appearance is marred or that subsequent surface treatments are adversely affected. Slip agents such as erucamide and oleamide can also be used.

Antistatic agents incorporated by internal means into thermoplastic resins are preferred in this invention and include nonionic materials such as quaternary ammonium compounds such as N,N-bis(2-hydroxyethyl) octadecylamine, N,N-bis(2-hydroxyethyl) tallow amine, bis(2-hydroxyethyl) stearylamine and ethoxylated alkylamine and polyol esters of monocarboxylic acids having 10 to 28 carbon atoms or mixtures of such acids. Suitable polyols from which these esters may be derived include ethylene glycol, propylene glycol, glycerol, pentaerythritol and like materials. Preferred esters include mixtures of mono-, di-, and triglycerides of monocarboxylic acids having 10 to 28 carbon atoms such as decanoic, lauric, myristic, palmitic and stearic acids, as well as mixtures of such esters. Most preferred esters are esters of monocarboxylic acids having 10 to 22 carbon atoms and are most preferably stearyl monoglycerides containing at least about 80 wt % glycerol monostearate monoester.

Particularly useful and preferred in this invention is the addition of glycerol monostearate (GMS) to polyolefin resins in melt form with these compositions used to produce the thermoplastic filaments that make up the uniform basis weight self-bonded nonwoven webs having improved antistat properties and increased softness. Advantages of internal melt-added GMS include improvement over topically treated or externally-applied antistatic agents because the water resistance of composite products comprising the self-bonded nonwoven webs with the internally added glycerol monostearate is retained for the most part or only marginally affected. Melt-added antistatic agents are also less expensive to add to the self-bonded nonwoven web and are longer lasting. For imparting antistatic properties to polyolefins self-bonded nonwoven webs such that the surface resistivity as determined by AATCC 76 is $10^{13}$ ohms/square or less, the preferred level of GMS is about 0.05 to about 1.0 wt %. When GMS is added to polyolefins such as polypropylene and used to form the self-bonded nonwoven webs, the resulting web surprisingly has improved softness as well as improved surface resistivity. For improved softness of polypropylene self-bonded nonwoven webs, preferred GMS levels are about 0.05 to about 0.5 wt %. Above levels of about 0.5 wt % GMS, polypropylene self-bonded nonwoven webs tend to exhibit an "oily" appearance which detracts from the appearance and usefulness of the web in many applications.

As used herein, terms such as "nonwoven web", "uniform basis weight", "self-bonded", and "substantially continuous" have definitions as defined below.

By "nonwoven web" it is meant a web of material which has been formed without the use of weaving processes and which has a construction of individual fibers, filaments or threads which are substantially randomly disposed.

By "uniform basis weight nonwoven web" it is meant a nonwoven web comprising a plurality of substantially randomly disposed, substantially continuous polymeric filaments having a Basis Weight Uniformity Index of 1.0±0.05 determined from average basis weights having standard deviations of less than 10%. BWUI is defined as a ratio of an average unit area basis weight determined on a unit area sample of web to an average basis weight determined on an area of web, N times as large as the unit area, wherein N is about 12 to about 18, the unit area is 1 $in^2$ and wherein standard deviations of the average unit area basis weight and the average basis weight are less than 10% and the number of samples is sufficient to obtain basis weights at a 0.95 confidence interval. As used herein for the determination of BWUI, both the average unit area basis weight and the average area basis weight must have standard deviations of less than 10% where "average" and "standard deviation" have the definitions generally ascribed to them by the science of statistics. Materials having BWUIs of 1.0±0.05, which are determined from average basis weights having standard deviations greater than 10% for one or both of the averages, do not represent a uniform basis weight nonwoven web as defined herein and are uneconomical or poorly suited for use in many applications because the nonuniformity of basis weights may require heavier basis weight materials to be used to obtain adequate coverage and fabric aesthetics. Unit area samples below about 1 $in^2$ in area for webs which have particularly nonuniform basis weight and coverage would represent areas too small to give a meaningful interpretation of the unit area basis weight of the web. The samples on which the basis weights are determined can be any convenient shape, such as square, circular, diamond and the like, with the samples randomly cut from the fabric by punch dies, scissors and the like to assure uniformity of the sample area size. The larger area is about 12 to about 18 times the area of the unit area. The larger area is required to obtain an average basis weight for the web which will tend to "average out" the thick and thin areas of the web. The BWUI is then calculated by determining the ratio of the average unit area basis weight to the average larger area basis weight. A BWUI of 1.0 indicates a web with a very uniform basis weight. Materials having BWUI values of less than 0.95 or more than 1.05 are not considered to have uniform basis weights as defined herein. Preferably, the BWUI has a value of 1.0±0.03.

By "self-bonded" it is meant that the crystalline and oriented filaments or fibers in the nonwoven web adhere to each other at their contact points thereby forming a self-bonded, fibrous nonwoven web. Adhesion of the fibers may be due to fusion of the hot fibers as they contact each other, to entanglement of the fibers with each other or to a combination of fusion and entanglement. However, all contact points of the fiber do not result in fibers fusing together. Generally, the adhesion of the fibers is such that the nonwoven web after being laid down but before further treatment has sufficient MD and CD strength to allow handling of the web without additional treatment. No foreign material is employed to promote bonding and essentially no polymer flows to the intersection points as distinguished from that which occurs during the heat-bonding of thermoplastic filaments. The bonds are weaker than the filaments as evidenced by the observation that an exertion of a force tending to disrupt the web, as in tufting, will fracture bonds before breaking filaments.

By "substantially continuous", in reference to the polymeric filaments of the webs, it is meant that a majority of the filaments or fibers formed by extrusion through orifices in the rotary die remain as continuous nonbroken fibers as they are drawn and then impacted on the collection device. Some fibers may be broken during the attenuation or drawing process, with a substantial majority of the fibers remaining continuous.

One suitable method of forming the uniform basis weight self-bonded, fibrous nonwoven web of substantially randomly disposed, substantially continuous polymeric filaments comprises the steps of:

(a) extruding a molten polymer through multiple orifices located in a rotating die,
(b) contacting the extruded polymer while molten as it exits the orifices with a fluid stream having a velocity of 70 m/s or greater to form substantially continuous filaments and to draw the filaments into fibers having deniers in the range of about 0.5 to about 20, and
(c) collecting the drawn fibers on a collection device whereby the filaments extruded through the die strike the collection device and self-bond to each other to form the nonwoven web.

In one embodiment of the process, the fluid stream is supplied by a fluid delivery system comprising a radial aspirator surrounding the rotary die with the aspirator having an outlet channel with an exit and a blower for providing fluid to the aspirator.

A source of liquid fiber forming material such as a thermoplastic melt is provided and pumped into a rotating die having a plurality of spinnerets about its periphery. The rotating die is rotated at an adjustable speed such that the periphery of the die has a spinning speed of about 2.5 to about 35 m/s, calculated by multiplying the periphery circumference by the rotating die rotation speed measured in revolutions per second.

The thermoplastic polymer melt is extruded through a plurality of spinnerets located about the circumference of the rotating die. There can be multiple spinning orifices per spinneret with the diameter of an individual spinning orifice between about 0.1 to about 2.5 mm preferably about 0.2 to about 1.0 mm. The length-to-diameter ratio of the spinneret diameter is about 1:1 to about 10:1. The particular geometrical configuration of the spinneret orifice can be circular, elliptical, star-shaped, Y-shaped, delta-shaped, multilobal or any other suitable configuration. Preferably, the configuration of the spinneret orifice is circular or trilobal. The rate of polymer extruded through the spinneret orifices measured in Kg/hr/orifice can range from about 0.02 to about 2.25 Kg/hr/orifice. Preferably, the rate is about 0.1 Kg/hr/orifice or greater.

As the fibers are extruded horizontally through spinneret orifices in the circumference of the rotating die, the fibers assume a helical orbit as they begin to fall below the rotating die. The fluid stream which contacts the fibers can be directed downward onto the fibers, can surround the fibers or can be directed essentially parallel to the extruded fibers. In one embodiment, a fluid delivery system having a radial aspirator surrounding the rotary die, with the aspirator having an outlet channel with an exit and a blower for providing fluid to the aspirator so that the velocity of the fluid at the exit of the outlet channel of the aspirator is about 70 m/s or greater. Preferably, the fluid is ambient air. The air can also be conditioned by heating, cooling, humidifying, or dehumidifying. The preferred velocity of the air at the exit of the outlet channel of the aspirator is about 100 to about 125 m/s. The blower can be a pressure air blower fan capable of generating over 635 mm of water gauge at volumetric flow rates of 1.4 m$^3$/s or more.

Polymer fibers extruded through the spinneret orifices of the rotary die are contacted by the quench air stream of the aspirator. The quench air stream can be directed around, above or essentially parallel to the extruded fibers. It is also contemplated to extrude the filaments into the air stream.

In one embodiment, the quench air stream is directed radially above the fibers which are drawn toward the high-velocity air stream as a result of a partial vacuum created in the area of the fiber by the air stream as it exits the aspirator. The polymer fibers then enter the high-velocity air stream and are drawn, quenched and transported to a collection surface. The high-velocity air, accelerated and distributed in a radial manner, contributes to the attenuation or drawing of the radially extruded thermoplastic melt fibers. The accelerated air velocities contribute to the placement or "laydown" of fibers onto a circular fiber collector surface or collector plate such that nonwoven webs are formed that exhibit improved properties including increased tensile strength, lower elongation, and more balanced physical properties in the MD and CD from fibers having deniers ranging from about 1.0 to about 3.0.

The fibers are conveyed to the collector plate at elevated air speeds of 70 m/s or greater to promote entanglement of the fibers for web integrity and produce a fibrous nonwoven web with more balanced strength properties in the machine direction and cross-machine direction, with a slight predominance in the machine direction tensile strength.

While the fibers are moving at a speed dependent upon the speed of rotation of the die as they are drawn down, by the time the fibers reach the outer diameter of the orbit, they are not moving circumferentially, but are merely being laid down in that particular orbit basically one on top of another. The particular orbit may change depending upon variation of rotational speed, extrudate input, temperature, etc. External forces such as electrostatic charge or air pressure may be used to alter the orbit and, therefore, deflect the fibers into different patterns.

The self-bonded, fibrous nonwoven webs are produced by allowing the extruded thermoplastic fibers to contact each other as the fibers are deposited on a collection surface. Many of the fibers, but not all, adhere to each other at their contact points thereby forming a self-bonded, fibrous nonwoven web. Adhesion of the fibers may be due to fusion of the hot fibers as they contact each other, to entanglement of the fibers with each other or to a combination of fusion and entanglement. Generally, the adhesion of the fibers is such that the nonwoven web after being laid down but before further treatment has sufficient MD and CD strength to allow handling of the web without additional treatment.

The nonwoven fabric will confirm to the shape of the collection surface. The collection surface can be of various shapes such as a cone-shaped inverted bucket, a moving screen or a flat surface in the shape of an annular strike plate located slightly below the elevation of the die and with the inner diameter of the annular strike plate being at an adjustable, lower elevation than the outer diameter of the strike plate.

When an annular strike plate is used as the collection surface, many of the fibers are bonded together during contact with each other and with the annular strike plate producing a nonwoven fabric which is drawn back through the aperture of the annular strike plate as a tubular fabric. A stationary spreader can be supported below the rotary die to spread the fabric into a flat two-ply composite which is collected by a pull roll and winder. In the alternative, a knife arrangement can be used to cut the tubular two-ply fabric into a single-ply fabric which can be collected by the pull roll and winder.

Temperature of the thermoplastic melt affects the process stability for the particular thermoplastic used. The temperature must be sufficiently high so as to enable drawdown, but not too high to allow excessive thermal degradation of the thermoplastic.

Process parameters which control the fiber formation from thermoplastic polymers include: the spinneret orifice design, dimension and number; the extrusion rate of polymer through the orifices; the quench air velocity; and the rotary die rotational speed. Fiber denier can be influenced by all of the above parameters with fiber denier typically increasing with larger spinneret orifices, higher extrusion rates per orifice, lower air quench velocity and lower rotary die rotation with other parameters remaining constant. Productivity is influenced by the dimension and number of spinneret orifices, the extrusion rate and for a given denier fiber the rotary die rotation.

The system provides process parameters whereby various fiber deniers can be attained simply by varying die rotation and/or pumping rate and/or air quench velocity. At a given die rotation, pumping rate and air quench velocity, the denier for individual filaments within a given web can range from about 0.5 to about 20 denier for 90% or greater of the fibers. For polypropylene this range of filament deniers corresponds to filament diameters in the range of about 5 to about 220 microns. Typically, the average value for filament denier is in the range of about 1 to about 7. For relatively high air quench velocities the average filament deniers are in range of about 1.0 to about 3.0 denier. Preferably the basis weight of the nonwoven webs formed from these filaments is about 3.5 gm$^2$ or greater.

The nonwoven webs exhibit balanced physical properties such that the ratio of the machine direction (MD) tensile strength to the cross direction (CD) tensile strength is close to 1. However, the MD/CD ratio can be varied by varying the quench air velocity to produce webs with predominantly MD or CD strength. Preferably, the ratio of MD to CD tensile strength is about 1:1 to about 1.5:1.

Any suitable thermoplastic polymer that can be melt-formed into filament or fiber can be used for making the self-bonded nonwoven webs of this invention. Illustrative of such polymers are synthetic linear polycarbonamides characterized by the presence of recurring carbonamide groups as an integral part of the polymer chain and separated from one another by at least two carbon atoms. Polyamides of this type include polymers, generally known in the art as nylons, obtained from diamines and dibasic acids having the recurring unit represented by the general formula:

—NHCORCONHR$^1$— in which R is an alkylene group of at least two carbon atoms, preferably from about 2 to about 10 carbon atoms or arylene, preferably substituted or unsubstituted phenylene; and R$^1$ is selected from R and phenyl groups. Also included are copolyamides and terpolyamides obtained by known methods, as for example, by condensation of hexamethylene diamine and a mixture of dibasic acids consisting of terephthalic acids and derivatives thereof, as for example, lactams, or acids such as aminobutyric acid, 6-aminohexanoic acid, 7-aminoheptanoic acid, 8-aminooctanoic acid, 9-aminononanoic acid, 11-aminoundecanoic acid, 12-aminododecanoic acid.

Polyamides of the above description are well known in the art and include, for example, a copolyamide of 30 mole % hexamethylene diammonium isophthalate and 70 mole % hexamethylene diammonium adipate, a copolyamide having up to 30 mole % bis-(p-amidocyclohexyl)methylene, terephthalic acid and caprolactan, poly(hexamethylene sebacamide), poly(hepta-methylene pimelamide), poly(octamethylene suberamide), poly(hexamethylene sebacamide), poly(nonamethylene azelamide), poly(decamethylene azelamide), poly(decamethylene sebacamide), polybis(4-amino-cyclohexylmethane-1,10-decanedicarboxamide), poly(m-xylylene adipamide), poly(p-xylylene sebacamide), poly(2,2,2-trimethylhexamethylene pimelamide), poly(piperazine sebacamide), poly(meta-phenylene isophthalamide), poly(p-phenylene terephthalamide), poly(hexamethylene isophthalamide), poly(hexamethylene terephthalamide), polycaproamide, or combinations thereof.

Other thermoplastic polymers which may be employed are linear polyesters having wide variations in physical properties. The particular polyester chosen can be a homopolyester or a co-polyester, or mixtures thereof as desired. Polyesters are normally prepared by the condensation of an organic dicarboxylic acid and an organic diol, and, therefore, illustrative examples of useful polyesters will be described hereinbelow in terms of these diol and dicarboxylic acid precursors. Polyesters which are suitable are those which are derived from the condensation of aromatic and cycloaliphatic dicarboxylic acids and may be cycloaliphatic, aliphatic or aromatic polyesters.

Exemplary of useful cycloaliphatic, aliphatic and aromatic polyesters are poly(ethylene terephthalate), poly(cyclohexylenedimethylene terephthalate), poly(lactide), poly(ethylene azelate), poly(butylene terephthalate), poly(ethylene 2,7-naphthalate), poly(ethylene succinate), poly(ethylene adipate), poly(ethylene sebacate), poly(decamethylene adipate), poly(decamethylene sebacate), poly(ethylene isophthalate), poly(tetramethylene terephthalate), poly(hexamethylene terephthalate), poly(decamethylene terephthalate), poly(ethylene 1,5-naphthalate), and poly(ethylene 2,6-naphthalate).

Polyester compounds which also are suitable are prepared from the condensation of a diol and an aromatic dicarboxylic acid are preferred for use in this invention. Illustrative of such useful aromatic carboxylic acids are terephthalic acid, isophthalic acid and an o-phthalic acid, 1,3-, 1,4-, 2,6- or 2,7-naphthalenedicarboxylic acid, 4,4'-diphenyl-dicarboxylic acid, 4,4'-diphenylsulphone-dicarboxylic acid, 1,1,3-trimethyl-5-carboxy(p-carboxyphenyl)-indane, diphenyl ether 4,4'-dicarboxylic acid, bis-p(carboxyphenyl)methane and the like. Of the aforementioned aromatic dicarboxylic acids based on a benzene ring, terephthalic acid, isophthalic acid, and orthophthalic acid are preferred for use and among these preferred acid precursors, terephthalic acid is particularly preferred.

Other polymers which may be used in this invention are polymers derived from unsaturated monomers of the formula:

R$_1$R$_2$C=CH$_2$ wherein R$_1$ and R$_2$ are the same or different and are hydrogen, alkyl, phenyl, alkoxyphenyl, halophenyl, alkylphenyl, haloalkyl, naphthyl, cyano, phenoxy, hydroxy, carboxy, alkanoyl, amino, halogen, amide, nitride, alkoxycarbonyl, phenol, alkylamino, alkoxy, alkoxyalkyl, dialkylamino, carbazole, phenylcarbonyl, phenoxycarbonyl and pyrrolidino.

Illustrative of such polymers are polyvinyl chloride, polyvinylene fluoride, polyacrylamide, polyacrylonitrile, polyvinyl pyridine, polyvinyl acetate, polyacrylic acid, polyvinyl pyrrolidine, polyvinyl methyl ether, polyvinyl formal, polystyrene, polyethylene, polypropylene, poly(1-octadecene), polyisobutylene, poly(1-pentene), poly(2-methylstyrene), poly(4-methylstyrene), poly(1-hexene), poly(5-methyl-1-hexene), poly(4-methyl-1-pentene), poly(1-butene), poly(3-methyl-1-butene), poly(3-phenyl-1-propene), polybutylene, poly(1-hexene), poly(5-methyl-1-hexene), poly(1-octadecene), poly(vinylcyclopentane), poly(vinylcyclohexane), poly(α-vinylnaphthalene), and the like.

The term "polyolefins" is meant to include homopolymers of branched and straight-chained olefins, copolymers prepared from at least 50 wt % of an unsaturated hydrocarbon monomer and blends of such polymers. The polyolefins of choice are those in which R$_1$ is hydrogen and R$_2$ is hydrogen or alkyl having from 1 to about 8 carbon atoms such as polyethylene, polypropylene, poly(isobutylene), poly(1-pentene), poly(3-methyl-1-butene), poly(1-hexene), poly(4-methyl-1-pentene), and poly(1-octene). Among these, particularly preferred polyolefins include polypropylene, ethylene-propylene random copolymer, linear low density polyethylene, blends of polypropylene and polybutene, and blends of polypropylene and linear low density polyethylene. Mixtures or blends of these thermoplastic resins and, optionally, thermoplastic elastomers such as polyurethanes, elastomeric polymers such as copolymers of an isolefin and a conjugated polyolefin, and copolymers of isobutylenes and the like can also be used.

The polypropylene used by itself or in blends with polybutene (PB) and/or linear low density polyethylene (LLDPE) preferably has a melt flow rate in the range of about 10 to about 80 g/10 min as measured by ASTM D-1238. Blends of polypropylene and polybutene and/or linear low density polyethylene provide self-bonded nonwoven webs with softer hand such that the web has greater flexibility and/or less stiffness.

The ethylene-propylene random copolymer can contain about 1.0 to about 5.0 wt % ethylene, preferably about 1.5 to 3.5 wt % ethylene. Such copolymers have a melt flow rate in the range of about 1 to about 40 g/10 min, as measured by ASTM D-1238.

The blends of polypropylene and PB can be formulated by metering PB in liquid form into a compounding extruder by any suitable metering device by which the amount of PB being metered into the extruder can be controlled. PB can be obtained in various molecular weight grades with high molecular weight grades typically requiring heating to reduce the viscosity for ease of transferring the PB. A stabilizer additive package can be added to the blend of polypropylene and PB if desired. Polybutenes suitable for use can have a number average molecular weight measured by vapor phase osmometry of about 300 to about 3000. The PB can be prepared by well-known techniques such as the Friedel-Crafts polymerization of feedstocks comprising isobutylene, or they can be purchased from a number of commercial suppliers such as Amoco Chemical Company, Chicago, Ill., which markets polybutenes under the tradename Indopol ®. A preferred number average molecular weight for PB is in the range of about 300 to about 2500.

The PB can be added directly to polypropylene or it can be added via a masterbatch prepared by adding PB to polypropylene at weight ratios of 0.2 to 0.3 based on polypropylene in a mixing device such as a compounding extruder with the resulting masterbatch blended with polypropylene in an amount to achieve a desired level of PB. The weight ratio of PB typically added to polypropylene can range from about 0.01 to about 0.15. When a weight ratio of PB below about 0.01 is added to polypropylene, little beneficial effects such as better hand and improved softness are shown in the blends, and when polybutene is added at a weight ratio above about 0.15, minute amounts of PB can migrate to the surface which may detract from the fabric appearance. Blends of polypropylene and PB can have a weight ratio of polypropylene in the range of about 0.99 to about 0.85, preferably about 0.99 to about 0.9, and a weight ratio of PB in the range of about 0.01 to about 0.15, preferably about 0.01 to about 0.10.

Blends of polypropylene and LLDPE can be formulated by blending polypropylene and LLDPE resins in the form of pellets or powder in a mixing device such as a drum tumbler and the like. The resin blend with an optional stabilizer additive package can be introduced to a polymer melt mixing device such as a compounding extruder of the type typically used to produce commercial polypropylene resin and compounded at temperatures between about 150° C. and about 260° C. Although blends of polypropylene and LLDPE can range from a weight ratio of nearly 1.0 for polypropylene to a weight ratio of nearly 1.0 for LLDPE, typically, blends of polypropylene and LLDPE useful for making the self-bonded nonwoven webs of the instant invention can have a weight ratio of polypropylene in the range of about 0.99 to about 0.85, preferably in the range of about 0.98 to about 0.92, and a weight ratio of LLDPE in the range of about 0.01 to about 0.15, preferably in the range of about 0.02 to about 0.08. For weight ratios of LLDPE less than 0.01 the softer hand properties imparted from the LLDPE are not obtained, and for weight ratios above 0.15 less desirable physical properties and a smaller processing window are obtained.

The LLDPE which can be used in making the self-bonded, fibrous nonwoven webs of the present invention can be random copolymers of ethylene with 1 to 15 wt % of higher olefin co-monomers such as propylene, n-butene-1, n-hexene-1, n-octene-1 or 4-methylpentene-1 produced over transition metal coordination catalysts. Such LLDPE can be produced by liquid phase or vapor phase processes. The preferred density of LLDPE is in the range of about 0.91 to about 0.94 g/cc.

Additives such as colorants, pigments, dyes, opacifiers such as $TiO_2$, UV stabilizers, fire retardant compositions, processing stabilizers and the like can be incorporated into the thermoplastic resins and blends.

The self-bonded nonwoven webs of this invention having improved antistatic and softness properties can be used in applications by themselves or as one or more layers of composite or laminate products. Such applications include but are not limited to coverstock for absorbent materials in the manufacture of diapers, incontinence pads, towel materials, wraps for surgical instruments, surgical caps, gowns, patient drapes, surgical table covers, isolation gowns, robe lining and facings, mattress pads, covers, tickings, shower curtains, drapes, drapery liners, pillow cases, bedspreads, quilts, sleeping bags, liners, weed control and seed/crop cover in the agricultural market, house wrap in the construction market, moist cloths such as wet wipes, oil wipes, medical wipes and hygiene wipes, wound pads and dressings, oil spill absorbents, recreational fabric applications including tents, outer wear, tarpaulins and the like.

Softness of the self-bonded nonwoven webs can be determined qualitatively by touch and in a more quantitative manner by using a KES-FB4 Surface Tester of Texmac, Inc., Charlotte, N.C., to determine the coefficient of friction and surface roughness. Preferably, for self-bonded nonwoven webs of this invention prepared from polymeric compositions comprising polypropylene and GMS, the surface roughness has a value of 8.5 or less as measured on a KES-FB4 Surface Tester.

In composite products, the self-bonded, fibrous nonwoven webs of this invention are preferably in the form of a composite product having improved antistatic, softness and retention of water resistant properties comprising at least one layer of a uniform basis weight self-bonded, fibrous nonwoven web comprising a plurality of substantially randomly disposed, substantially continuous polymeric filaments comprising glycerol monostearate and a thermoplastic selected from the group consisting of polypropylene, ethylenepropylene random copolymer, a blend of polypropylene and polybutene, and a blend of polypropylene and linear low density polyethylene wherein said web has a Basis Weight Uniformity Index of 1.0±0.05 determined from average basis weights having standard deviations of less than 10% and the web is adhered to at least one layer of a material selected from the group consisting of porous film having a moisture vapor transmission rate of 100 $g/m^2/24$ hr or greater as measured by ASTM E-96, procedure E, impervious film, woven fabric, polymeric foam and nonwoven fabric. The fabric layer can be a nonwoven fabric selected from the group selected from the group consisting of meltblown fabrics, spunbond fabrics and carded web fabrics. Other types of materials useful as composite layers include woven, warp knitted or stitch bonded fabrics, metallic foils, flexible and scrim or rigid foam and net-like web materials such as CLAF®.

The layers of the composite can be adhered to each other by any suitable bonding technique used in woven and nonwoven technology including thermal bonding, ultra-sonic bonding, point embossing, chemical adhesive or solvent bonding and mechanical bonding such as needle punching. Bonding parameters for thermal bonding such as temperature, pressure, dwell time in the nip, number of bonds or indentations per unit area and percent area coverage are determined by the thermoplastic materials used and by the characteristics desired in the finished product. Composite products combine the soft, static resistant and very uniform basis weight nonwoven webs of the present invention with one or more distinct materials.

In the alternative because the nonwoven webs of the present invention have a very uniform basis weight and improved physical properties as well as softness and static resistant properties, the web can be used by itself without further processing. Preferred in this invention is a uniform basis weight self-bonded, fibrous nonwoven web having improved softness and antistatic properties comprising a plurality of substantially randomly disposed, substantially continuous polymeric filaments comprising an effective amount of glycerol monostearate and a thermoplastic selected from the group consisting of polypropylene, ethylene-propylene random copolymer, high density polyethylene, low density polyethylene, linear low density polyethylene, a blend of polypropylene and polybutene, and a blend of polypropylene and linear low density polyethylene wherein said web has a basis weight of about 3.5 g/m$^2$ or greater, a Basis Weight Uniformity Index of 1.0±0.05 determined from average basis weights having standard deviations of less than 10% and a surface resistivity of about 1.0×10$^{13}$ ohms/square or less. Processes typically used in the production of nonwoven webs such as calendering, embossing, uniaxial and biaxial stretching can be used in post-treatment of the nonwoven webs of the present invention.

Composites of this invention comprising one or more layers of the self-bonded nonwoven webs formed from filaments comprising GMS and a polypropylene-based resin exhibit antistatic and softness properties as well as the retention of water resistance properties as measured by hydrostatic resistance and impact penetration. Composites prepared from webs having externally-added antistatic agents tend to exhibit improved antistatic properties with diminished retention of water resistance properties.

While the invented webs exhibit web uniformity approaching that of conventional meltblown webs, there are significant differences including the invented web's substantially continuous filaments and relatively high strength as opposed to meltblown's lower strength.

The self-bonded, nonwoven web can be supplied directly from the process described above or from product wound on an unwind roll. The self-bonded nonwoven web can be either a single-ply or a multi-ply nonwoven web. Typically, a two-ply web is used such that a layer of a self-bonded web having a nominal basis weight of 7 g/m$^2$ or greater comprises two plies of a self-bonded web each having a nominal basis weight of 3.5 g/m$^2$ or greater. The two-ply self-bonded web enhances the excellent uniform basis weight of the single plies that make up the two-ply, self-bonded nonwoven webs. The self-bonded, nonwoven web can have post-treatment, such as thermal bonding, point-bonding and the like. One embodiment produces a two-ply, nonwoven web of the present invention and uses no post-treatment before the web is used to form composite structures.

Test procedures used to determine the properties reported for the Examples are listed below:

Tensile and Elongation—Test specimens are used to determine tensile strength and elongation according to ASTM Test Method D-1682. Grab tensile strength can be measured in MD on 1 inch wide samples of the fabric or in the CD and is reported in units of lbs. A high value is desired for tensile strength.

Elongation can also be measured in the MD or in the CD and is reported in units of %.

Trapezoidal Tear Strength—The trapezoidal tear strength is determined by ASTM Test Method D-1117.14 and can be measured in the MD or in the CD and is reported in units of lbs with a high value desired.

Fiber Denier—The fiber diameter is determined by comparing a fiber specimen sample to a calibrated reticule under a microscope with suitable magnification. From known polymer densities, the fiber denier is calculated.

Impact Penetration—The impact penetration was determined by AATCC Test Method 42-1985 with a low value desired.

Hydrostatic Resistance—The hydrostatic resistance was determined by AATCC Test Method 127-1989 with a high value desired.

Surface Resistivity—The surface resistivity was determined by AATCC Test Method 76 with a low value desired.

Mason Jar Test—The mason jar test was determined by IST 80.7 with a longer time desired.

Coefficient of Friction, Surface Roughness and Bending Results—The coefficient of friction, mean deviation of coefficient of friction and surface roughness were determined on a KES-FB4 Surface Tester and the bending rigidity and recovery from bending were determined on a KES-FB2 Bending Shearer Tester. Both testers are by Texmac, Inc., 3001 Stafford Drive, Charlotte, N.C. 28266-8128.

Basis Weight—The basis weight for a test sample is determined by ASTM Test Method D 3776 option C.

Basis Weight Uniformity Index—The BWUI is determined for a nonwoven web by cutting a number of unit area and larger area samples from the nonwoven web. The method of cutting can range from the use of scissors to stamping out unit areas of material with a die which will produce a consistently uniform unit area sample of nonwoven web. The shape of the unit area sample can be square, circular, diamond or any other convenient shape. The unit area is 1 in$^2$, and the number of samples is sufficient to give a 0.95 confidence interval for the weight of the samples. Typically, the number of samples can range from about 40 to 80. From the same nonwoven web an equivalent number of larger area samples are cut and weighed. The larger samples are obtained with appropriate equipment with the samples having areas which are N times larger than the unit area samples, where N is about 12 to about 18. The average basis weight is calculated for both the unit area sample and the larger area sample, with the BWUI ratio determined from the average basis weight of the unit area divided by the average basis weight of the larger area. Materials which have unit area and/or area average basis weights determined with standard deviations greater than 10% are not considered to have uniform basis weights as defined herein.

The following examples further illustrate the present invention, although it will be understood that these examples are for purposes of illustration, and are not intended to limit the scope of the invention.

EXAMPLE 1

A masterbatch of polypropylene containing 10 wt % glycerol monostearate (GMS) was prepared by dry blending polypropylene powder having a nominal melt flow rate (MFR) of 2.0 g/10 min with glycerol monostearate, Dimodan PM from Grindsted Products Inc., in the form of dry powder at room temperature, in a drum mixer/blender. Sufficient GMS was used to produce a masterbatch having 10 wt % GMS together with processing additives and sufficient peroxide component to obtain a masterbatch composition having a MFR of 34.4 g/10 min. A polypropylene composition containing 0.3 wt % GMS was prepared from a polypropylene resin having a nominal MFR of 35 g/10 min and an appropriate amount of the above-described GMS masterbatch letdown with a 2.0 g/10 min MFR polypropylene to obtain a concentration of 0.3 wt % GMS in the final product and was extruded at a constant rate through circular spinneret orifices in a rotating die. The process conditions were:

| Extrusion temperature, °C. | Zone - 1 | 216 |
| --- | --- | --- |
| | Zone - 2 | 298 |
| | Zone - 3 | 294 |
| | Zone - 4 | 292 |
| | Zone - 5 | 294 |
| | Zone - 6 | 293 |
| | Adapter | 295 |
| | Rotary union | 294 |
| | Die | 214 |
| Extruder screw, rpm | | 55 |
| Upstream pressure, psi | | 1,120 |
| Melt pressure, psi | | 265 |
| Die rotation, rpm | | 2400 |
| Extrudate rate, Kg/hr/orifice | | 0.26 |

The uniform basis weight, self-bonded, fibrous nonwoven product of Example 1 in the form of a two-ply web had a basis weight of 25.5 g/m$^2$ and was calendered at a rate of 0.81 m/s using a 56 cm calender having a steel smooth roll maintained at 129° C. temperature and a steel embossing roll maintained at 127° C. temperature and at a pressure of 300 pounds per linear inch (pli). The bonding area of the embossing roll was 16% of the total area with 256 points per in$^2$ (ppi). Five samples of the self-bonded nonwoven web were tested for coefficient of friction, surface roughness, bending rigidity and recovery from bending. The results of the five tests were averaged and an average value for each of the measured parameters was calculated with the highest and lowest values excluded. The results and calculated averages are summarized in Table 1.

TABLE 1

| | Coefficient of Friction, Surface Roughness and Bending Results | | | | |
| --- | --- | --- | --- | --- | --- |
| Sample No. | Coefficient of Friction | Mean Deviation of Coefficient of Friction | Surface Roughness | Bending Rigidity | Recovery from Bending |
| 1 | 0.264 | 0.0305 | 9.05 | 0.0387 | 0.0208 |
| 2 | 0.223 | 0.0273 | 8.18 | 0.0300 | 0.0184 |
| 3 | 0.227 | 0.0260 | 6.44 | 0.0314 | 0.0200 |
| 4 | 0.214 | 0.0292 | 7.27 | 0.0390 | 0.0238 |
| 5 | 0.230 | 0.0283 | 8.38 | 0.0249 | 0.0236 |
| Average of five sample values | 0.232 | 0.0282 | 7.86 | 0.0328 | 0.0213 |
| Average excluding high & low values | 0.227 | 0.0282 | 7.94 | 0.0333 | 0.0214 |

EXAMPLE 2

A uniform basis weight self-bonded nonwoven web having a basis weight of 25.5 g/m$^2$ (nominal 0.75 oz-/yd$^2$) was prepared from a polypropylene composition containing 0.4 wt % GMS using process, operating and calendering conditions as described in Example 1. Five samples of the self-bonded nonwoven web were tested for coefficient of friction, mean deviation of coefficient of friction, surface roughness, bending rigidity and recovery from bending. The results together with the calculated average of five sample values and the average of five sample values excluding the high and low values are summarized in Table II.

TABLE 1

| | Coefficient of Friction, Surface Roughness and Bending Results | | | | |
| --- | --- | --- | --- | --- | --- |
| Sample No. | Coefficient of Friction | Mean Deviation of Coefficient of Friction | Surface Roughness | Bending Rigidity | Recovery from Bending |
| 1 | 0.203 | 0.0296 | 9.17 | 0.0511 | 0.0256 |
| 2 | 0.223 | 0.0280 | 7.54 | 0.0263 | 0.0189 |
| 3 | 0.234 | 0.0300 | 8.50 | 0.0330 | 0.0178 |
| 4 | 0.234 | 0.0276 | 7.77 | 0.0346 | 0.0180 |
| 5 | 0.232 | 0.0254 | 7.18 | 0.0276 | 0.0178 |
| Average of five sample values | 0.225 | 0.0281 | 8.03 | 0.0345 | 0.0196 |
| Average excluding | 0.230 | 0.0284 | 7.94 | 0.0317 | 0.0182 |

TABLE 1-continued

Coefficient of Friction, Surface Roughness and Bending Results

| Sample No. | Coefficient of Friction | Mean Deviation of Coefficient of Friction | Surface Roughness | Bending Rigidity | Recovery from Bending |
|---|---|---|---|---|---|
| high & low values | | | | | |

The BWUI was determined from 60 samples of 1 inch×1 inch squares and 60 samples of 4 inch×4 inch squares cut and weighed for basis weight. The basis weight of the 1×1 squares was 0.75 oz/yd$^2$ with a standard deviation of 0.04 (5.3%) and the basis weight of the 4×4 squares was 0.75 oz/yd$^2$ with a standard deviation of 0.02 (2.7%). A BWUI value of 1.000 was calculated.

COMPARATIVE EXAMPLE A

A uniform basis weight self-bonded nonwoven web having a basis weight of 25.5 g/m$^2$ was prepared from a polypropylene composition having no GMS and a nominal MFR of 35 g/10 min using process, operating and calendering conditions as described in Example 1. Five samples of the self-bonded nonwoven web were tested for coefficient of friction, mean deviation of coefficient of friction, surface roughness, bending rigidity and recovery from bending. The results together with the calculated average of five sample values and the average of five sample values excluding the high and low values are summarized in Table III.

TABLE 1

Coefficient of Friction, Surface Roughness and Bending Results

| Sample No. | Coefficient of Friction | Mean Deviation of Coefficient of Friction | Surface Roughness | Bending Rigidity | Recovery from Bending |
|---|---|---|---|---|---|
| 1 | 0.242 | 0.0306 | 9.49 | 0.0404 | 0.0216 |
| 2 | 0.260 | 0.0356 | 10.14 | 0.0385 | 0.0235 |
| 3 | 0.277 | 0.0316 | 10.12 | 0.0396 | 0.0227 |
| 4 | 0.271 | 0.0334 | 9.06 | 0.0398 | 0.0215 |
| 5 | 0.248 | 0.0352 | 9.79 | 0.0325 | 0.0222 |
| Average of five sample values | 0.260 | 0.0333 | 9.72 | 0.0382 | 0.0223 |
| Average excluding high & low values | 0.260 | 0.0334 | 9.80 | 0.0394 | 0.0222 |

In comparing Examples 1 and 2 with Comparative Example A, the value of the coefficient of friction for Examples 1 and 2 are 11.5 and 12.7% lower than for the coefficient of friction value for Comparative Example A. Also, the surface roughness of Examples 1 and 2 is 19.0% lower than the surface roughness of Comparative Example A. These reductions in coefficient of friction and surface roughness exhibited by the Examples containing GMS indicate an improved softness of these self-bonded nonwoven webs.

EXAMPLE 3 AND COMPARATIVE EXAMPLE B

Three-layer nonwoven fabric composites were made utilizing two layers of uniform basis weight self-bonded nonwoven webs produced by process conditions similar to those described in Example 1 for the outer two layers and a meltblown microfibrous fabric as the intermediate layer. The self-bonded nonwoven webs had a two-ply structure with a nominal basis weight per ply of 8.5 g/m$^2$ and a nominal total basis weight of 17 g/m$^2$ with the web wound onto a roll. The microfibrous fabric was a polypropylene meltblown nonwoven fabric available from Ergon, wound on a roll with a basis weight of 12.9 g/m$^2$ and blue or white in color. The self-bonded nonwoven webs used as the outer layers and the meltblown fabric used as the intermediate layer were uniformly fed from roll stock through a 56 cm wide calender with a hard steel, embossed calender roll maintained at a temperature of 129° C. and a hard steel, anvil calender roll maintained at a temperature of 127° C. The bonding area of the embossing roll was 16 percent of the total surface area of the roll. A pressure of 300 pli was maintained on the three layers of fabric to thermally bond the layers together to form the three-layer composite nonwoven fabric at a speed of 0.81 m/s. Example 3a had outer layers of white self-bonded nonwoven web fabric prepared from a polypropylene composition having a concentration of 0.2 wt % GMS and an inner layer of blue meltblown fabric. Example 3b had outer layers of white self-bonded nonwoven web fabric prepared from a polypropylene composition having a concentration of 0.3 wt % GMS and an inner layer of white meltblown fabric. Example 3c had outer layers of white self-bonded nonwoven web fabric prepared from a polypropylene composition having a concentration of 0.4 wt % GMS and an inner layer of blue meltblown fabric. Comparative Example B had outer layers of white self-bonded nonwoven web fabric prepared from a polypropylene composition having no added GMS and an inner layer of white meltblown fabric. For Examples 3a-3c and Comparative Example B, the basis weight, grab strength, elongation, hydrostatic resistance, water impact penetration, surface resistivity and the Mason Jar test were determined and are summarized in Table IV.

TABLE IV

Composite Properties

| Property | Example 3a | Example 3b | Example 3c | Comparative Example B |
|---|---|---|---|---|
| Basis Weight, g/m$^2$ | 46.8 | 40.7 | 45.8 | 45.8 |
| Grab Strength, lb | | | | |
| MD | 12.0 | 12.3 | 11.9 | 14.8 |
| CD | 13.9 | 13.5 | 12.8 | 14.6 |
| Elongation, % | | | | |
| MD | 52 | 60 | 51 | 49 |
| CD | 116 | 137 | 93 | 111 |
| Hydrostatic Resistance, cm | 58.4 | 37.6 | 48.3 | 52.6 |

TABLE IV-continued

| | Composite Properties | | | |
|---|---|---|---|---|
| | Example | | | Comparative |
| Property | 3a | 3b | 3c | Example B |
| Impact Resistance, g | 7.3 | 8.9 | 4.3 | 0.2 |
| Resistivity, ohm/square | $10^{11}$ | $10^{10}$–$10^{11}$ | $10^{12}$ | $10^{15}$ |
| Mason Jar Test, min | 10 | <1 | <10 | >60 |

MD — Machine Direction
CD — Cross-machine Direction

TABLE V

| | Composite Properties | | | | |
|---|---|---|---|---|---|
| | Example | | | | Comparative Example |
| Property | 4a | 4b | 4c | 4d | C |
| Hydrostatic Resistance, cm | 18.5 | 21.1 | 26.2 | 27.4 | 69.9 |
| Impact Penetration, g | 4.4 | 5.0 | 0.1 | 0.0 | 0.0 |
| Static Decay, sec. | <3 | <3 | <3 | <3 | >300 |

EXAMPLE 4 AND COMPARATIVE EXAMPLE C

Three-layer nonwoven fabric composites were made utilizing two layers of uniform basis weight self-bonded nonwoven webs produced by process conditions similar to those described in Example 1 for the outer two layers and a meltblown microfibrous fabric as the intermediate layer. The self-bonded nonwoven web had a two-ply structure with a nominal basis weight per ply of 6 g/m$^2$ and a nominal total basis weight of 12 g/m$^2$ with the web wound onto rolls. The microfibrous fabric was a polypropylene meltblown nonwoven fabric available from Ergon wound on a roll and had a basis weight of 12.9 g/m$^2$. The two rolls of self-bonded nonwoven web used as outer layers and a roll of meltblown fabric used as the intermediate layer were uniformly fed through a 56 cm wide calender with a hard steel, embossed calender roll maintained at a temperature of 129° C. and a hard steel, anvil calender roll maintained at a temperature of 127° C. The bonding area of the embossing roll was 16 percent of the total surface area of the roll. A pressure of 300 pli was maintained on the three layers of fabric to thermally bond the layers together to form the three-layer composite with a nominal basis weight of 37.3 g/m$^2$ at a speed of 0.81 m/s. Example 4a had an antistat composition of 50 wt % of Zelec DP, a polymeric quaternary ammonium salt antistatic agent available from DuPont, and 50 wt % FC-808, a fluorochemical emulsion available from 3M Company, sprayed on the composite with an add-on solids content of 2.6 wt % achieved on the composite after the composite was dried for 15 seconds in an IR oven set at 135° C. Example 4b had an antistat composition of 40 wt % Zelec DP, 20 wt % FC-808 and 40 wt % mineral oil sprayed on the composite with an add-on solids content of 2.7 wt % achieved on the composite after the composite was dried for 15 seconds in an IR oven set at 135° C. Example 4c had an antistat composition of 40 wt % Zelec DP, 40 wt % FC-808 and 20 wt % mineral oil sprayed on the composite with an add-on solids content of 0.6 wt % achieved on the composite after the composite was dried for 15 seconds in an IR oven set at 135° C. Example 4d had an antistat composition of 50 wt % of Zelec DP and 50 wt % mineral oil sprayed on the composite with an add-on content of 0.7 wt % solids achieved on the composite after the composite was dried for 15 seconds in an IR oven set at 135° C. Comparative Example C had no antistat composition sprayed on the composite. Hydrostatic resistance, water impact penetration and the static decay using a Rothschild Static Voltmeter Model R-4021 are summarized in Table V.

EXAMPLE 5

A three-layer nonwoven fabric composite was made utilizing two layers of uniform basis weight self-bonded nonwoven webs made from polypropylene containing 0.2 wt % GMS by process conditions according to those described in Example 1 for the outer two layers and a meltblown microfibrous fabric as the intermediate layer. The 0.2 wt % GMS-containing polypropylene was prepared by weigh-feeding GMS masterbatch and polypropylene powder into a compounding extruder. The self-bonded nonwoven webs had a two-ply structure with a basis weight per ply of about 14.95 g/m$^2$ and a total basis weight of 29.9 g/m$^2$ with the web wound onto a roll. The microfibrous fabric was a white meltblown nonwoven fabric available from Ergon, made of polypropylene, wound on a roll and had a basis weight of 14.95 g/m$^2$. The self-bonded nonwoven webs used as the outer layers and the meltblown fabric used as the intermediate layer were uniformly fed from roll stock through a 56 cm wide calender with a steel, embossed calender roll maintained at a temperature of 121° C. and a steel, anvil calender roll maintained at a temperature of 118° C. The embossing roll had a bonding area of 16 percent of the total surface area of the roll and had 196 points per in$^2$ (ppi). A pressure of 300 pli was maintained on the three layers of fabric to thermally bond the layers together to form the three-layer composite nonwoven fabric at a speed of 0.81 m/s. The basis weight, grab strength, elongation, trap tear, hydrostatic resistance, water impact penetration and surface resistivity were determined and are summarized in Table VI.

COMPARATIVE EXAMPLE D

A three-layer nonwoven fabric composite was made utilizing two layers of uniform basis weight self-bonded nonwoven webs made from polypropylene containing no GMS by process conditions according to those described in Example 1 for the outer two layers and a meltblown microfibrous fabric as the intermediate layer. The self-bonded nonwoven webs had a two-ply structure with a basis weight per ply of about 14.95 g/m$^2$ and a total basis weight of 29.9 g/m$^2$ with the web wound onto a roll. The microfibrous fabric was a white meltblown nonwoven fabric available from Ergon, made of polypropylene, wound on a roll and had a basis weight of 14.95 g/m$^2$. The self-bonded nonwoven webs used as the outer layers and the meltblown fabric used as the intermediate layer were uniformly fed from roll stock through a 56 cm wide calender with a steel, embossed calender roll maintained at a temperature of 121° C. and a steel, anvil calender roll maintained at a temperature of 118° C. The embossing roll had a bonding area of 16 percent of the total surface area of the roll and had 196 points per in$^2$ (ppi). A pressure of 300 pli was maintained on the three layers of fabric to thermally bond the layers together to form the three-layer composite nonwoven fabric at a speed of 0.81 m/s. The basis weight, grab strength, elongation, trap tear, hydrostatic resistance, water impact penetration, and resistivity properties for the composites are summarized in Table VI.

TABLE VI

| | Composite Properties | |
|---|---|---|
| Property | Example 5 | Comparative Example D |
| Basis Weight, g/m$^2$ | 60.1 | 60.4 |
| Grab Strength, lb | | |
| MD | 74 | 61 |
| CD | 173 | 190 |
| Trap Tear, lbs | | |
| MD | 16.8 | 14.0 |
| CD | 11.1 | 11.3 |
| Hydrostatic Resistance, cm | 67.1 | 54.4 |
| Impact Penetration, g | 0.0 | 0.8 |
| Resistivity, ohms/square | 10$^{13}$ | 10$^{16}$ |

MD — Machine Direction
CD — Cross-machine Direction

The water resistance properties of Example 5 were improved compared to Comparative Example D as well as the composites of Example 4 with externally applied antistatic agents.

EXAMPLE 6

A two-layer nonwoven fabric composite having a basis weight of 22.4 g/m$^2$ was made by the process, calendering and operating conditions of Example 5 with 0.2 wt % GMS-containing polypropylene used to prepare the self-bonded nonwoven web having a basis weight of 9.5 g/m$^2$ and the meltblown nonwoven fabric had a basis weight of 12.9 g/m$^2$. Table VII summarizes the water resistance properties for composite aging studies of Examples 5 and 6.

TABLE VII

| | Composite Aging Studies Water Resistance Properties | | | |
|---|---|---|---|---|
| | Example 5 | | Example 6 | |
| | Days Since Production | Value | Days Since Production | Value |
| Impact Penetration, g | 12 | 0.0 | 12 | 5.4 |
| | 36 | 0.0 | 36 | 5.3 |
| | 62 | 0.0 | 62 | 3.1 |
| | 83 | 0.0 | | |
| Hydrostatic Resistance, cm | 12 | 63.9 | 12 | 54.1 |
| | 36 | 67.1 | 36 | 53.3 |
| | 62 | 63.2 | 62 | 56.4 |
| | 83 | 63.8 | | |
| Resistivity, ohms/square | 12 | 10$^{13}$ | 12 | 10$^{13}$ |
| | 36 | 10$^{13}$ | 36 | 10$^{13}$ |
| | 62 | 10$^{13}$ | 62 | 10$^{13}$ |
| | 83 | 10$^{14}$ | | |

EXAMPLE 7

Uniform basis weight self-bonded nonwoven webs were produced by the process, operating and calendering conditions as described in Example 1 for polypropylenes having 0.025, 0.113 and 0.2 wt % of GMS. The resistivity of these webs were:

| GMS level, wt % | Resistivity, ohms/square |
|---|---|
| 0.025 | 10$^{16}$ |
| 0.113 | 10$^{13}$ |
| 0.200 | 10$^{12}$ |

EXAMPLE 8 AND COMPARATIVE EXAMPLE E

Uniform basis weight self-bonded nonwoven webs were produced by the process, operating and calendering conditions as described in Example 1 using an ethylene-propylene random copolymer having a 3.3 wt % ethylene content and 0.2 wt % GMS. Basis weight, impact penetration, hydrostatic resistance and resistivity values as determined for two different basis weight examples of Example 8, Examples 8a and 8b, compared with Control Example E, a uniform basis weight self-bonded nonwoven web prepared from polypropylene and no GMS, are summarized in Table VIII.

TABLE VIII

| | Self-Bonded Nonwoven Web Properties | | |
|---|---|---|---|
| Property | Example 8a | Example 8b | Control E |
| Basis Weight, g/m$^2$ | 34.0 | 25.5 | 34.0 |
| Impact Penetration, g | 15.9 | 15.9 | 14.6 |
| Hydrostatic Resistance, cm | 9.9 | 12.7 | 16.0 |
| Resisitivity, ohms/square | 10$^{13}$ | 10$^{12}$ | 10$^{16}$ |

The BWUI was determined for a higher basis weight example, Example 8c, with 60 samples of 1 inch×1 inch squares and 60 samples of 4 inch×4 inch squares cut and weighed for basis weight. The basis weight of the 1×1 squares was 1.19 oz/yd$^2$ with a standard deviation of 0.05 (4.2%) and the basis weight of the 4×4 squares was 1.15 oz/yd$^2$ with a standard deviation of 0.02 (1.7%). A BWUI value of 1.035 was calculated.

That which is claimed is:

1. A uniform basis weight self-bonded, fibrous nonwoven web having improved antistatic properties comprising a plurality of substantially randomly disposed, substantially continuous polymeric filaments comprising a polyolefin resin having incorporated therein an antistatic agent in an amount effective to provide a web having surface resistivity of about $1.0 \times 10^{13}$ ohms/square or less without substantial adverse surface effect on the web, said web having a Basis Weight Uniformity Index of $1.0 \pm 0.05$ determined from average basis weights having standard deviations of less than 10% wherein said Basis Weight Uniformity Index is defined as a ratio of an average basis weight determined on a unit area of 1 in$^2$ sample of web to an average basis weight determined on an area of web 12 to 18 times as large as the unit area.

2. The web of claim 1 wherein said polymeric filaments comprise a polyolefin composition selected from the group consisting of polypropylene, ethylene-propylene random copolymer, high density polyethylene, low density polyethylene, linear low density polyethylene, a blend of polypropylene and polybutene, and a blend of polypropylene and linear low density polyethylene.

3. The web of claim 1 wherein said antistatic agent is selected from the group consisting of N,N-bis(2-hydroxyethyl) octadecylamine, N,N-bis (2-hydroxyethyl) tallow amine, bis(2-hydroxyethyl) stearylamine and polyol ester of a monocarboxylic acid having 10 to 28 carbon atoms.

4. The web of claim 3 wherein said polymeric filaments comprise a polyolefin composition selected from the group consisting of polypropylene, ethylene-propylene random copolymer having about 1.0 to about 5.0 wt % ethylene, high density polyethylene, low density polyethylene, linear low density polyethylene, a blend of polypropylene and polybutene, and a blend of polypropylene and linear low density polyethylene, and said antistatic agent comprises about 0.05 to about 1.0 wt % glycerol monostearate.

5. A uniform basis weight self-bonded, fibrous nonwoven web having improved softness and antistatic properties comprising a plurality of substantially randomly disposed, substantially continuous polymeric filaments comprising a polyolefin resin selected from the group consisting of polypropylene, ethylene-propylene random copolymer, high density polyethylene, low density polyethylene, linear low density polyethylene, a blend of polypropylene and polybutene, and a blend of polypropylene and linear low density polyethylene, said polyolefin resin having incorporated therein about 0.05 to about 1.0 wt. % glycerol monostearate such that said web has a surface resistivity of about $1.0 \times 10^{13}$ ohms/square or less wherein said web has a Basis Weight Uniformity Index of $1.0 \pm 0.05$ determined from average basis weights having standard deviations of less than 10% wherein said Basis Weight Uniformity Index is defined as a ratio of an average basis weight determined on a unit area of 1 in$^2$ sample of web to an average basis weight determined on an area of web 12 to 18 times as large as the unit area.

6. The nonwoven web of claim 5 wherein said polymeric filaments comprise an ethylene-propylene random copolymer having about 1.0 to about 5.0 wt % ethylene and about 0.05 to about 1.0 wt % glycerol monostearate.

7. The nonwoven web of claim 5 wherein said polymeric filaments comprise a polypropylene having a melt flow rate in the range of about 10 to about 80 g/10 min as measured by ASTM D-1238 and about 0.05 to about 0.5 wt % glycerol monostearate.

* * * * *